United States Patent [19]
Wootton

[11] Patent Number: 4,492,613
[45] Date of Patent: Jan. 8, 1985

[54] RECOVERY OF COMPONENTS OF A BINARY AZEOTROPE

[75] Inventor: Gerald V. Wootton, Akron, Ohio

[73] Assignee: The B. F. Goodrich Company, Akron, Ohio

[21] Appl. No.: 404,157

[22] Filed: Aug. 2, 1982

[51] Int. Cl.³ .............................................. B01D 3/36
[52] U.S. Cl. ...................................... 203/39; 203/71; 203/98; 203/DIG. 19; 203/DIG. 9; 202/176; 202/204; 568/913
[58] Field of Search ...................... 203/39, 71, 81, 66, 203/63, 98, DIG. 19, DIG. 9; 202/204, 176; 568/913; 528/496

[56] References Cited

U.S. PATENT DOCUMENTS

| | | | |
|---|---|---|---|
| 2,341,433 | 2/1944 | Fisher | 203/66 |
| 2,368,050 | 1/1945 | Tooke | 203/66 |
| 2,423,795 | 7/1947 | Patterson | 203/39 |
| 3,271,273 | 9/1966 | Fox et al. | 203/39 |
| 3,434,937 | 3/1969 | Elliott et al. | 568/913 |
| 3,480,516 | 11/1969 | Tindall et al. | 203/66 |
| 4,161,429 | 7/1979 | Baiel et al. | 568/913 |
| 4,400,501 | 8/1983 | Lane, Jr. et al. | 528/496 |

FOREIGN PATENT DOCUMENTS 525468  5/1956  Canada ............................... 203/66

OTHER PUBLICATIONS

Technique of Organic Chemistry, vol. IV, Distillation Weissberger, 1951, (pp. 366–368).

Primary Examiner—Wilbur Bascomb
Assistant Examiner—V. Manoharan
Attorney, Agent, or Firm—George A. Kap; Nestor W. Shust

[57] ABSTRACT

Methanol and cyclohexane are recovered from a condensed methanol-cyclohexane azeotrope by allowing the condensed azeotrope to separate in a vessel into an upper phase rich in cyclohexane and a lower phase rich in methanol, fractionating the upper phase in a first column whereby the methanol-cyclohexane azeotrope is taken off the top and returned to the vessel while cyclohexane is removed from the lower portion of the first column, and fractionating the lower phase in a second column whereby the methanol-cyclohexane azeotrope is taken off the top and returned to the vessel while methanol is removed from the lower portion of the second column.

14 Claims, 2 Drawing Figures

RECOVERY OF COMPONENTS OF A BINARY AZEOTROPE

BACKGROUND OF THE INVENTION

In the solution ring opening polymerization of cycloolefins, the product discharged from the reactor is a honey-like cement that consists principally of a nonpolar solvent in which the polymer is dissolved. The polymer content in the cement is normally on the order of about 15% by weight. The polymer can be any of the family of polymers that are made by polymerizing one or more of cycloolefins that contain the norbornene group.

After the honey-like cement is obtained, it is necessary to separate the polymer from the nonpolar solvent. This is accomplished by mixing in a high shear mixer about three volumes of a nonsolvent to about one volume of cement whereby the polymer precipitates out. A nonsolvent is a liquid that is miscible with the nonpolar solvent, however, the polymer is insoluble in the nonsolvent. Examples of suitable nonsolvents include methanol, ethanol, n-propanol, isopropanol, etc.

When polymer cement is mixed with a nonsolvent, the polymer coagulates or precipitates out of the solvent-nonsolvent liquid medium whereas the oligomers, catalyst residues, and other by-products and impurities remain solubilized therein. Thus, the precipitation procedure also performs the function of purifying the polymer. Polymer recovery in this manner, however, produces large volumes of contaminated liquid composed primarily of a nonsolvent, nonpolar solvent, and by-products and impurities. Solvent recovery from the large volumes of solvent-nonsolvent liquid is difficult and expensive, and is especially complicated when water extraction is employed and when water-free nonsolvents are used that form azeotropes with water.

Prior to precipitation of the polymer from cement, however, the cement can be preconcentrated from about 15% solids to 20 to 35% solids and above. Like precipitation, preconcentration is accomplished with a nonsolvent and the only critical difference being the amount of nonsolvent used. Whereas in precipitation about 2 to 6 volumes of nonsolvent is used to 1 volume of cement, in preconcentration, about 5 to 100 parts of nonsolvent is used per 100 parts of cement, on volume basis. Generally speaking, the amount of nonsolvent should be sufficient to preconcentrate but insufficient to precipitate the polymer. In preconcentration, the nonsolvent extracts a substantial portion of the solvent and impurities from the cement causing formation of a gel-like substance of increased viscosity having a higher polymer content.

U.S. patent application Ser. No. 376,368 entitled "Anhydrous Precipitation of Polycycloolefins" was filed May 10, 1982 for inventors Lane, Tenney and Wootton, now U.S. Pat. No. 4,400,501 issued Aug. 23, 1983. That patent is directed to precipitation of polycycloolefins from cements containing the polymer dissolved in cyclohexane solvent by the use of methanol as the nonsolvent. The precipitation approach disclosed in that application is based on the fact that, when boiled, cyclohexane and methanol form an azeotrope which separates into two phases on condensation, the upper phase being essentially cyclohexane and the lower phase being rich in methanol.

SUMMARY OF THE INVENTION

In a preferred embodiment, this invention relates to separation of cyclohexane and methanol from the condensed azeotrope of cyclohexane and methanol in a vessel that separates into a lower phase rich in methanol and an upper phase that is essentially all cyclohexane by conveying the upper phase to a first fractionating column, removing from the top of the first column the azeotrope of cyclohexane and methanol and returning it to the vessel while removing cyclohexane from the bottom of the first column, conveying the lower phase from the vessel to a second fractionating column, removing the azeotrope of cyclohexane and methanol from the top of the second column and returning it to the vessel while removing methanol from the bottom of the second column.

DETAILED DESCRIPTION OF THE INVENTION

Generally, the invention disclosed herein is applicable to any binary liquid system yielding an azeotrope when boiled, which, when condensed, separates into two liquid phases each of which is preferentially rich in one or the other of the binary components in comparison with the azeotrope. More specifically, this invention relates to a process for recovering methanol and cyclohexane from a condensed azeotrope of methanol and cyclohexane comprising the steps of introducing the condensed azeotrope into a decanter vessel where the azeotrope forms an upper phase rich in cyclohexane and a lower phase rich in methanol, conveying the upper phase to a first distillation column, withdrawing methanol-cyclohexane azeotrope from the upper portion of the first column and cyclohexane from the lower portion of the same column, conveying the lower phase to a second distillation column and withdrawing methanol cyclohexane azeotrope from the upper portion of the second column and methanol from the lower portion of the same column.

Methanol and cyclohexane are unique in their relationship with each other. No other azeotrope of an alcohol and cyclohexane separates into two phases on condensation without water addition.

Solutions of cyclohexane and methanol are obtained from precipitation of polycycloolefins from polymer cements and from preconcentration of polymer cements. In a precipitation operation that is carried out at an elevated temperature, polymer cement is mixed with a large volume of cyclohexane, on the order of 3 to 10 volumes of methanol to 1 volume of cement, and heated to drive off the azeotrope of methanol and cyclohexane that boils at 54° C. This azeotrope is composed of 37% methanol and 63% cyclohexane, on weight basis. However, solutions of methanol and cyclohexane can also be obtained from precipitation operation carried out at ambient conditions in which case, the solutions of methanol and cyclohexane will have varying composition depending on amount of methanol employed in the precipitation operation.

When the solutions of methanol and cyclohexane are obtained from a preconcentration operation, they contain much less methanol relative to cyclohexane since only up to about one volume of methanol is used to one volume of cement in such an operation.

Figure 2:
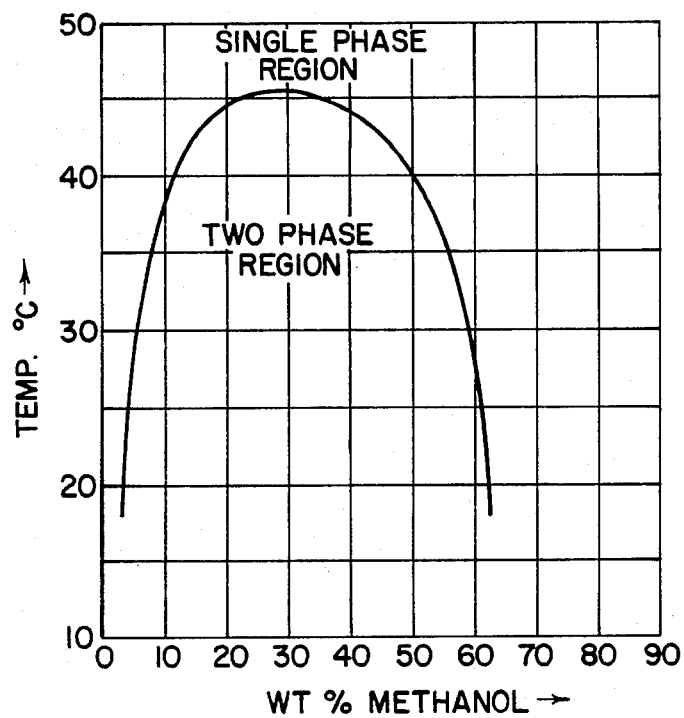
FIG. 2 is a coexistence curve for the cyclohexane-methanol system showing temperature dependence of the two phase system.

This invention relates to separation or recovery of methanol and cyclohexane from condensed azeotropes of methanol and cyclohexane that are obtained from polycycloolefin precipitation operations carried out at elevated temperature whereby the azeotrope is distilled off. This invention also relates to recovery of methanol and cyclohexane from solutions of methanol and cyclohexane. Although methanol and cyclohexane are miscible only to a limited extent, depending on temperature and composition as shown in FIG. 2, the mixtures of the two will be referred to herein as solutions regardless whether they are in fact solutions or physical mixtures.

Figure 1:
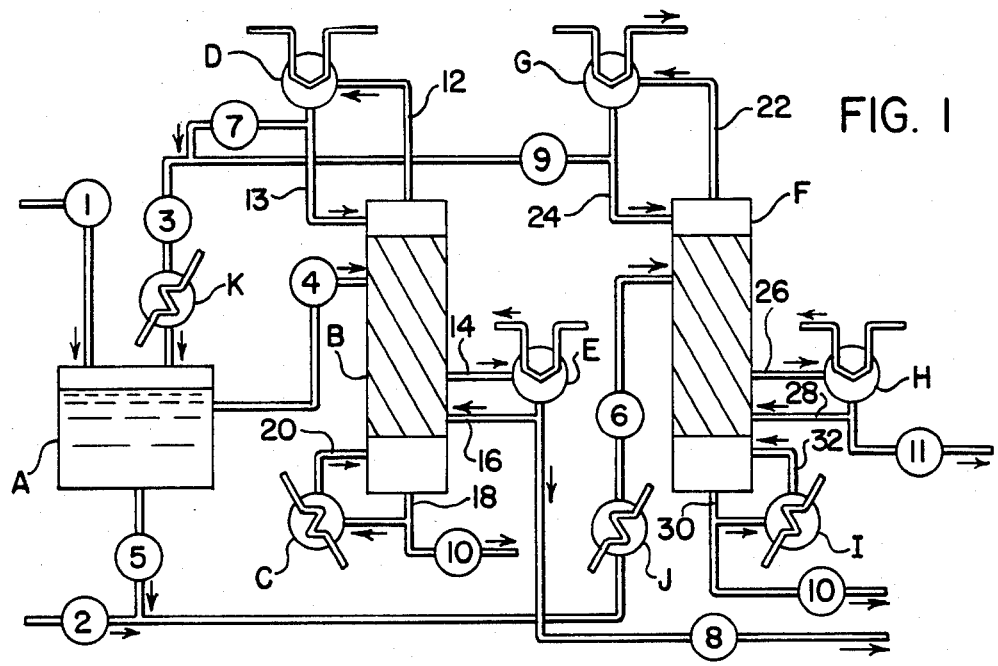
FIG. 1 is a flow diagram that illustrates recovery of methanol and cyclohexane from condensed azeotropes thereof.

The process of recovering methanol and cyclohexane is depicted in FIG. 1 which also illustrates the optional recovery of methanol and cyclohexane from a solution of methanol and cyclohexane that is obtained from a preconcentration operation of a polycycloolefin cement.

Referring to FIG. 1, line 1 conveys condensed azeotrope to decanter tank A. The azeotrope is composed of 37% methanol and 63% cyclohexane, on weight basis, that boils at 54° C. The azeotrope stream comes from a precipitation operation where a large volume of methanol is mixed with a polymer cement at an elevated temperature whereby the azeotrope is distilled off as a vapor and is then condensed. The condensed azeotrope is introduced into decanter A where it separates into two phases on standing for about one-half hour. The phase split in the decanter tank is 43% upper phase and 57% lower phase, on volume basis at 20° C. The cyclohexane-rich upper phase is composed of only 3% methanol and 97% cyclohexane whereas the lower phase, being methanolrich, is composed of 61% methanol and 39% cyclohexane. These figures are on weight basis measured at 20° C.

The upper phase in decanter tank A is conveyed via line 4 to fractionation column B provided with a reboiler C which provides the necessary heat for operating the fractionation column. Since the boiling point of cyclohexane at atmospheric pressure is about 80° C. whereas the boiling point of methanol is about 65° C. and that of the methanol-cyclohexane azeotrope is 54° C., the azeotrope is distilled-off at the top, condensed in condenser D to a temperature below 54° C. but sufficiently high to ensure that it remains in a single phase state, part of which is returned to decanter tank A and the remainder is recycled to column B as reflux via line 13. Based on the two-phase diagram in FIG. 2, the condensate temperature should be above about 46° C. The azeotrope in vapor state from column B is conveyed to the condenser via line 12 and from the condenser via line 7 it is combined with condensed azeotrope in line 3 and cooled by cooler K to ensure that two phases are formed before it is introduced into the decanter tank. Once in the decanter tank, the condensed azeotrope distributes itself between the upper and lower phases in the predetermined ratio.

Since cyclohexane boils higher than the methanol-cyclohexane azeotrope and methanol, it is withdrawn as a separate stream in vapor state through line 14 at the lower portion of column B. Cyclohexane is then condensed in condenser E and part of it is recycled to column B via line 16 whereas remainder is pumped via line 8 to a polymerization reactor where cycloolefin monomers containing the norbornene group are polymerized in presence of a ring opening catalyst and cyclohexane, as the solvent. The bottoms are removed from column B through line 18 and a portion thereof is recirculated through reboiler C and line 20 to the column whereas the remainder is considered waste and is pumped out through line 10.

Recovery of cyclohexane from the upper phase is accomplished with relative ease in the manner described. Since the upper phase in the decanter tank contains only 3% methanol, it should be apparent that methanol is quickly depleted from the system by vaporizing the azeotrope of methanol and cyclohexane that is composed of 37% methanol and 63% cyclohexane.

The lower phase from decanter tank A is conveyed to fractionation column F by means of line 5. In the embodiment illustrated in FIG. 1, a solution of methanol and cyclohexane from a preconcentration operation is introduced through line 2 and combined in line 6 with the lower phase in line 5 from the decanter tank. The combined stream is heated to about 50° C. by heater J to insure a single phase solution being fed to column F. In column F, the azeotrope of methanol and cyclohexane, boiling at 54° C., is removed from the top of the column through line 22, condensed in condenser G to a temperature below 54° C. but sufficiently high to insure that it remains in single phase state, part of it is returned to decanter tank A via line 9 and cooled, as described, to a two-phase state by cooler K, and the remainder is recycled as a single phase to the column via line 24. Methanol, boiling at about 65° C., is removed at the lower portion of column F through line 26, condensed in condenser H, and part of it is recycled to the column via line 28 and remainder is pumped to preconcentration and precipitation operations via line 11. The bottoms from column F are removed through line 30 with a portion of it being condensed in condenser I and recycled to the column via line 32 whereas remainder is taken to waste through line 10.

As already disclosed, the lower phase in decanter tank A is composed of 61% methanol and 39% cyclohexane. The solution of methanol and cyclohexane in line 2 is taken from a preconcentration operation and is also rich in methanol. Fractionation in column F is carried out in such a manner as to deplete essentially all cyclohexane by distilling a sufficient amount of the azeotrope. Since the azeotrope is composed of 37% methanol and 63% cyclohexane, it is apparent that cyclohexane is depleted almost twice as rapidly as methanol, which allows for withdrawal of a substantial quantity of methanol through line 26.

The azeotrope and the solutions of methanol and cyclohexane treated as described herein also contain small amounts of a molecular weight modifier that is added in the polymerization recipe of cycloolefins. Amount of the modifier used is at a level of about 0.0001 to 1 mole per 1 mole of the monomer charge and suitable modifiers are selected from nonconjugated acyclic olefins, especially alpha olefins such as 1-butane, 1-hexane, 1-heptene, and 1-octane. If 1-hexene (b.p. 63° C.) is used as the molecular modifier, it forms an azeotrope with methanol which boils at about 48° C. Since this is below the boiling temperature of the methanol-cyclohexane azeotrope (b.p. 54° C.), it would be taken off the top and would concentrate in the decanter tank. For this reason, it is preferred to use a molecular weight modifier with a higher boiling point than 1-hexene, such as 1-heptene or 1-octene. For instance, 1-octene boils at about 121° C. and, if used as a molecular weight modifier, would be taken off with cyclohexene at the lower portion of the column.

Data for the recovery process described above is given in Table I, below, where the streams are identified by numbers given in FIG. 1 and amounts thereof are given in parts by weight per hour.

TABLE I

| Components | Stream Number | | | | | | | | | | |
|---|---|---|---|---|---|---|---|---|---|---|---|
| | 1 | 2 | 3 | 4 | 5 | 6 | 7 | 8 | 9 | 10 | 11 |
| Methanol | 205 | 300 | 342 | 18 | 531 | 831 | 18 | | 324 | | 505 |
| Cyclohexane and Modifier | 350 | 215 | 582 | 593 | 339 | 554 | 28 | 565 | 554 | | Trace |

The above table does not indicate the level of impurities that are present in the streams identified above. The level of impurities varies from about 1% to a trace and the impurities that are present include molecular weight modifier, oligomers, catalyst residues, and unreacted monomers.

I claim:

1. A process for the separation and recovery of methanol and cyclohexane liquids from a mixture of methanol and cyclohexane comprising the steps of introducing into a decanter vessel a condensed azeotrope of methanol and cyclohexane, separating the phases into upper and lower liquid phases by decantation in the decanter vessel, conveying each phase to a separate distillation column, distilling the azeotrope from the upper portion of each column, condensing the azeotrope from each column, returning the condensed azeotrope to the decanter vessel, and recovering methanol, the lower boiling liquid, from the lower portion of one column and cyclohexane, the higher boiling liquid, from the lower portion of the other column.

2. Process of claim 1 wherein the process comprises the steps of introducing the condensed azeotrope into the decanter vessel where the azeotrope forms an upper phase rich in cyclohexane and a lower phase rich in methanol, conveying the upper phase to a first distillation column, withdrawing methanol-cyclohexane azeotrope from the upper portion of the first column and cyclohexane from the lower portion of the same column, conveying the lower phase to a second distillation column and withdrawing methanol-cyclohexane azeotrope from the upper portion of the second column and methanol from the lower portion of the same column.

3. Process of claim 2 wherein the azeotrope is composed of about 37% methanol and 63% cyclohexane, on weight basis, and boils at about 54° C. at atmospheric pressure.

4. Process of claim 2 wherein the phase split on volume basis at 20° C. is about 43% upper phase composed of about 3% by weight methanol and about 97% by weight cyclohexane, and about 57% lower phase composed of about 61% by weight methanol and about 39% by weight cyclohexane.

5. Process of claim 4 including the steps of condensing azeotrope from the first and second columns and recycling a portion of the condensed azeotrope to each respective column as reflux while returning the remainder of the condensed azeotrope from each column to the decanter vessel, and withdrawing the bottoms from each distillation column through the bottom of each column.

6. Process of claim 5 including the steps of withdrawing the bottoms from the first column that boil above cyclohexane, passing a portion of the bottoms to a reboiler and recycling that portion to the lower portion of the first column while removing remainder of the bottoms from the process; withdrawing the bottoms from the second column that boil above methanol, passing a portion of the bottoms to a reboiler and recycling that portion to the lower portion of the second column while removing remainder of the bottoms from the process.

7. Process of claim 5 including the steps of condensing the cyclohexane from the first column and recycling a portion thereof to the first column as reflux while withdrawing remainder of the cyclohexane from the process; condensing the methanol from the second column and recycling a portion thereof as reflux to the second column while withdrawing remainder of the methanol from the process.

8. Process of claim 7 wherein the temperature of the condensed azeotrope is maintained sufficiently high to insure that overhead reflux streams returned to the respective columns are single phase liquids and wherein the mixture consists essentially of methanol and cyclohexane.

9. Process of claim 7 wherein the condensed azeotrope from the respective columns returning to the decanter vessel is cooled to insure that it forms two phases before entering the decanter vessel.

10. Process of claim 7 including the steps of additionally introducing into the second column a solution of methanol and cyclohexane.

11. Process of claim 7 wherein the condensed azeotrope in the decanter vessel contains a small amount of a molecular weight modifier.

12. Process of claim 7 wherein the condensed azeotrope contains a small amount of a molecular weight modifier that boils above 63° C.

13. Process of claim 10 including the steps of combining the solution of methanol and cyclohexane and the lower phase from the decanter vessel to form a combined mixture and preheating the combined mixture to a temperature sufficient to insure that the combined mixture enters the second column as a single phase liquid.

14. Process of claim 11 including the step of withdrawing essentially all of the molecular weight modifier with cyclohexane from the first column.

* * * * *